US008084054B2

(12) United States Patent
Kabra et al.

(10) Patent No.: US 8,084,054 B2
(45) Date of Patent: Dec. 27, 2011

(54) BIOERODIBLE FILM FOR OPHTHALMIC DRUG DELIVERY

(75) Inventors: Bhagwati P. Kabra, Arlington, TX (US); Janet D. Howie, Keller, TX (US); Youqin Tian, Colleyville, TX (US); David Allen Marsh, Fort Worth, TX (US); Gustav Graff, Cleburne, TX (US)

(73) Assignee: Novartis AG, Basel (CH)

( * ) Notice: Subject to any disclaimer, the term of this patent is extended or adjusted under 35 U.S.C. 154(b) by 2267 days.

(21) Appl. No.: 10/610,090

(22) Filed: Jun. 30, 2003

(65) Prior Publication Data
US 2004/0126408 A1 Jul. 1, 2004

Related U.S. Application Data

(60) Provisional application No. 60/395,840, filed on Jul. 15, 2002, provisional application No. 60/432,721, filed on Dec. 12, 2002.

(51) Int. Cl.
*A61F 2/00* (2006.01)
(52) U.S. Cl. .................................. 424/426
(58) Field of Classification Search ................ 424/426
See application file for complete search history.

(56) References Cited

U.S. PATENT DOCUMENTS

| 4,344,968 A | 8/1982 | Aoda et al. |
| 4,786,495 A | 11/1988 | Bird et al. |
| 4,865,846 A | 9/1989 | Kaufman ............... 424/428 |
| 4,880,636 A * | 11/1989 | Franz ...................... 424/480 |
| 5,362,478 A | 11/1994 | Desai et al. ................. 424/9 |
| 5,433,951 A | 7/1995 | Serajuddin et al. |
| 5,439,686 A | 8/1995 | Desai et al. ............... 424/451 |
| 5,473,055 A | 12/1995 | Mongelli et al. ......... 530/329 |
| 5,484,608 A * | 1/1996 | Rudnic et al. ............ 424/468 |
| 5,498,421 A | 3/1996 | Grinstaff et al. ......... 424/450 |
| 5,504,102 A | 4/1996 | Agharkar et al. ......... 514/449 |
| 5,569,720 A | 10/1996 | Mongelli et al. ....... 525/329.4 |
| 5,614,549 A | 3/1997 | Greenwald et al. ....... 514/449 |
| 5,626,862 A | 5/1997 | Brem et al. ................ 424/426 |
| 5,651,986 A | 7/1997 | Brem et al. ................ 424/484 |
| 5,665,382 A | 9/1997 | Grinstaff et al. ......... 424/450 |
| 5,716,981 A * | 2/1998 | Hunter et al. ............. 514/449 |
| 5,719,265 A | 2/1998 | Mongelli et al. ......... 530/329 |
| 5,736,152 A | 4/1998 | Dunn ...................... 424/426 |
| 5,783,178 A | 7/1998 | Kabanov et al. ........ 424/78.31 |
| 5,886,026 A | 3/1999 | Hunter et al. ............ 514/449 |
| 5,888,493 A * | 3/1999 | Sawaya .................. 424/78.04 |
| 5,916,596 A | 6/1999 | Desai et al. ............... 424/489 |
| 5,994,341 A | 11/1999 | Hunter et al. ............ 514/210 |
| 6,004,573 A | 12/1999 | Rathi et al. ............... 424/426 |
| 6,017,948 A | 1/2000 | Rubinfeld et al. ........ 514/449 |
| 6,063,116 A | 5/2000 | Kelleher ..................... 623/4 |
| 6,096,331 A | 8/2000 | Desai et al. ............... 424/422 |
| 6,117,425 A | 9/2000 | MacPhee et al. ........ 424/94.64 |
| 6,146,659 A | 11/2000 | Rahman .................... 424/450 |
| 6,306,120 B1 | 10/2001 | Tan ........................... 604/294 |
| 6,369,116 B1 | 4/2002 | Wong et al. ............... 514/913 |
| 6,375,963 B1 * | 4/2002 | Repka et al. .............. 424/402 |
| 6,491,948 B1 * | 12/2002 | Buchholz et al. ......... 424/468 |
| 6,525,214 B1 | 2/2003 | Armitage et al. |
| 2002/0192280 A1 * | 12/2002 | Hunter et al. ............. 424/465 |
| 2004/0058313 A1 * | 3/2004 | Abreu ......................... 435/5 |

FOREIGN PATENT DOCUMENTS

| RU | 2086218 | 8/1997 |
| WO | WO 97/45105 | 12/1997 |
| WO | WO 99/00113 | 1/1999 |
| WO | WO 99/21908 | 5/1999 |
| WO | WO 00/64437 | 11/2000 |
| WO | WO 01/89522 | 11/2001 |

OTHER PUBLICATIONS

Taxol (Neil Edwards) Feb. 1996. Retrieved from the world wide web at www.chm.bris.ac.uk/motm/taxol/taxol.htm on May 3, 2006.*
Triacetin disclosure, downloaded from the world wide web at www.chemicalland21.com/industrialchem/plasticizer/TRIACETIN.hgm on Jan. 22, 2007.*
Cavalli et al. "Preparation and characterizatin of solid lipid nanospheres containing paclitaxel" European Journal fo Pharmaceutical Sciences 10 (2000) 305-309.*
Polyoxyethylene (40) Stearate disclosure, downloaded from the world wide web on Apr. 7, 2008.*
Polyoxyethylene (40) Stearate MSDS, downloaded from the world wide web on Apr. 7, 2008.*
Hamdani et al., "Physical and thermal characterisation of Precirol® and Comptirol® as lipophlic glycerides used for the preparation of controlled-release matrix pellets," *International J. of Pharmaceutics*, vol. 260, pp. 47-57 (2003).
Blandford et al., "Subconjunctival Sustained Release 5-Fluorouracil," *Investigative Ophthalmology & Visual Science*, vol. 33(12), pp. 3430-3435 (1992).
Borisuth et al., "The Risk Profile of Glaucoma Filtration Surgery," *Current Opin. Ophthalmology*, vol. 10; pp. 112-116 (1999).
Chang et al., "Basic Science and Clinical Aspects of Wound Healing in Glaucoma Filtering Surgery," *J. of Ocular Pharmacology*, vol. 14(1), pp. 75-95 (1998).
Charles et al., "Use of Bioerodible Polymers Impregnated with Mitomycin in Glaucoma Filtration Surgery in Rabbits," *Ophthalmology*, vol. 98(4), pp. 503-508 (1991).
Daniels et al., "Taxol Treatemtn of Experimental Proliferative Vitreoretinopathy," *Graefe's Archive Clin. Exp. Ophthalmology*, vol. 228, pp. 513-516 (1990).
Dukes et al., "The Use of Daunorubicin-Impregnated Bioerodible Polymers in Glaucoma Filtration Surgery in the Rabbit Model," *Investigative Ophthalmology & Visual Science*, vol. 33, p. 1391 (1992).
Greenfield et al., "Endophthalmitis After Filtering Surgery with Mitomycin," *Archives Ophthalmology*, vol. 114, pp. 943-949 (1996).
Jampel et al., Filtration Surgery in the Glaucomatous Non-Human Primate Using Polyanhydride Disks Containing Fluoroudine (FUR), *Investigative Ophthalmology & Visual Science*, vol. 30, p. 417 (1989).

(Continued)

*Primary Examiner* — Michael G Hartley
(74) *Attorney, Agent, or Firm* — Scott A. Chapple

(57) ABSTRACT

Drug delivery film compositions containing a combination of a water-soluble, film-forming polymers and a fatty acid glyceride or ester are suitable for delivering ophthalmic drugs.

20 Claims, 4 Drawing Sheets

OTHER PUBLICATIONS

Jampel et al., "Glaucoma Filtration Surgery in Monkeys Using 5-Fluorouridine in Polyanhydride Disks," *Archives of Ophthalmology*, vol. 108; pp. 430-435 (1990).

Jampel et al., "Glaucoma Filtration Surgery in Nonhuman Primates Using Taxol and Etoposide in Polyanhydride Carriers," *Investigative Ophthalmology & Vis. Science*, vol. 34(11), pp. 3076-3083 (1993).

Jampel et al., "Impact of Adjuvant Chemotherapy on Glaucoma Filtration Surgery," *J. of Glaucoma*, vol. 2; pp. 58-63 (1993).

Jampel et al., "In Vitro Release of Hydrophobic Drugs from Polyanhydride Disks," *Ophthalmic Surgery*, vol. 22(11), pp. 676-680 (1991).

Jampel et al, "The Effect of Paclitaxel Powder on Glaucoma Filtration Surgery in Rabbits," *J. of Glaucoma*, vol. 7, pp. 170-177 (1998).

Lanigan et al., "Single Intraoperative Applications of 5-fluorouracil during Filtration Surgery: Early Results," *British J. of Ophthalmology*, vol. 78, pp. 33-37 (1994).

Lee et al., "Effects of Cytosine Arabinoside-Impregnated Bioerodible Polymers on Glaucoma Filtration Surgery in Rabbits," *J. of Glaucoma*, vol. 2; pp. 96-100 (1993).

Lee et al., "Glaucoma Filtration Surgery in Rabbits Using Bioerodible Polymers and 5-Fluorouracil," *Ophthalmology*, vol. 94(12); pp. 1523-1530 (1987).

Lee et al, "The Use of Bioerodible Polymers and 5-Fluorouracil in Glaucoma Filtration Surgery,"*Investigative Ophthalmology & Visual Science*, vol. 29 (11); pp. 1692-1697 (1998).

Park et al., "Biodegradable Polyanhydride Devices of Cefazolin Sodium, Bupivacaine, and Taxol for Local and Drug Delivery: Preparation, and Kinetics and Mechanism of In Vitro Release," *J. Control Release*, vol. 52, pp. 179-189 (1998).

Rabowsky et al., "The Use of Bioerodible Polymers and Daunorubicin in Glaucoma Filtration Surgery," *Ophthalmology*, vol. 103(5); pp. 800-807 (1996).

Robin et al., "A Long-Term Dose-Response Study of Mitomycin in Glaucoma Filtration Surgery," *Archives Ophthalmology*, vol. 115, pp. 969-974 (1997).

Smith et al., "Drainage Tube Implantation with Intraoperative Mitomycin-C Application," *Invest. Oph. & Vis. Science*, vol. 34(4), p. 731 (1993).

Spaeth et al., "Argon Laser Trabeculoplasty Controls One Third of Cases of Progressive, Uncontrolled, Open Angle Glaucoma for 5 Years," *Archives Ophthalmology*, Vol. 110, pp. 491-494 (1992).

Uppal et al., "Pharmacokinetics of Etoposide Delivery by a Bioerodible Drug Carrier Implanted at Glaucoma Surgery," *J. of Ocular Pharmacology*, vol. 10(2), pp. 471-479 (1994).

Wilkins et al., "Antimetabolites," *Seminars in Ophthalmology*, vol. 12(3), pp. 143-151 (1997).

WuDunn et al., "Combined Penetrating Keratoplasty and Trabeculectomy with Mitomycin C," *Ophthalmology*, vol. 106(2), pp. 396-400n(1999).

Deshpande et al., "Bioerodible Polymers for Ocular Drug Delivery," *Critical Reviews in Therapeutic Drug Carrier Systems*, vol. 15(4); pp. 381-420 (1998).

Hatefi et al., "Biodegradable injectable in situ forming drug delivery systems," *J. of Controlled Release*, vol. 80; pp. 9-28 (2002).

* cited by examiner

BIOERODIBLE FILM FOR OPHTHALMIC DRUG DELIVERY

This application claims priority to U.S. Provisional Applications, U.S. Ser. No. 60/395,840 filed Jul. 15, 2002, and U.S. Ser. No. 60/432,721, filed Dec. 12, 2002.

BACKGROUND OF THE INVENTION

This invention relates to drug delivery compositions. In particular, this invention relates to the use of bioerodible materials as drug delivery films that are particularly useful in ophthalmic drug delivery. The drug delivery films of the present invention are especially suited for delivering anti-proliferative agents, such as paclitaxel or camptothecin, to maintain bleb function in glaucoma filtration surgery.

Paclitaxel or "taxol" has reportedly been used to maintain bleb function in glaucoma filtration surgery. Paclitaxel has been delivered in films prepared from biodegradable polymers, such as polyanhydrides or polylactides) or from non-degradable, non-erodible polymers, such as ethylene vinyl acetate. The disadvantage with biodegradable polymers is that it is difficult to biodegrade them in very short period, e.g., less than one week. Non-biodegradable, non-erodible drug dosage forms either stay forever, or have to be removed surgically.

Anti-proliferative agents used in connection with glaucoma filtration surgery have been delivered to the eye using bioerodible polymers. See, for example, Lee, et al., Ophthalmology 103(5):800-807 (May 1996). See also, Lee et al., Investigative Ophthalmology & Visual Science 29:1692-1697 (1988); and Uppal, et al., J. Ocular Pharmacology, 10(2):471-479 (1994).

What are needed are improved bioerodible drug delivery films that are suitable for delivering drugs to the eye.

SUMMARY OF THE INVENTION

The present invention provides bioerodible drug delivery films that are particularly suitable for ophthalmic drug delivery. The film compositions contain (i) a water-soluble, film-forming polymer and (ii) a fatty acid glyceride or ester. The drug delivery films are suitable for delivering any ophthalmically acceptable drug and are especially useful as subconjunctival or sub-Tenon's implants.

The drug delivery films of the present invention are more flexible than bioerodible films containing a water-soluble, film-forming polymer and lacking a fatty acid glyceride or ester. Without intending to be bound to any theory, it is believed that the fatty acid glyceride or ester ingredient slows dissolution of the film and may slow release of drug from the film.

One additional advantage that the drug delivery films of the present invention possess is that they are bioadhesive and, when used in connection with glaucoma filtration surgery to deliver an anti-proliferative agent, do not require suturing to maintain their position after implantation.

DETAILED DESCRIPTION OF THE INVENTION

Figure 1:
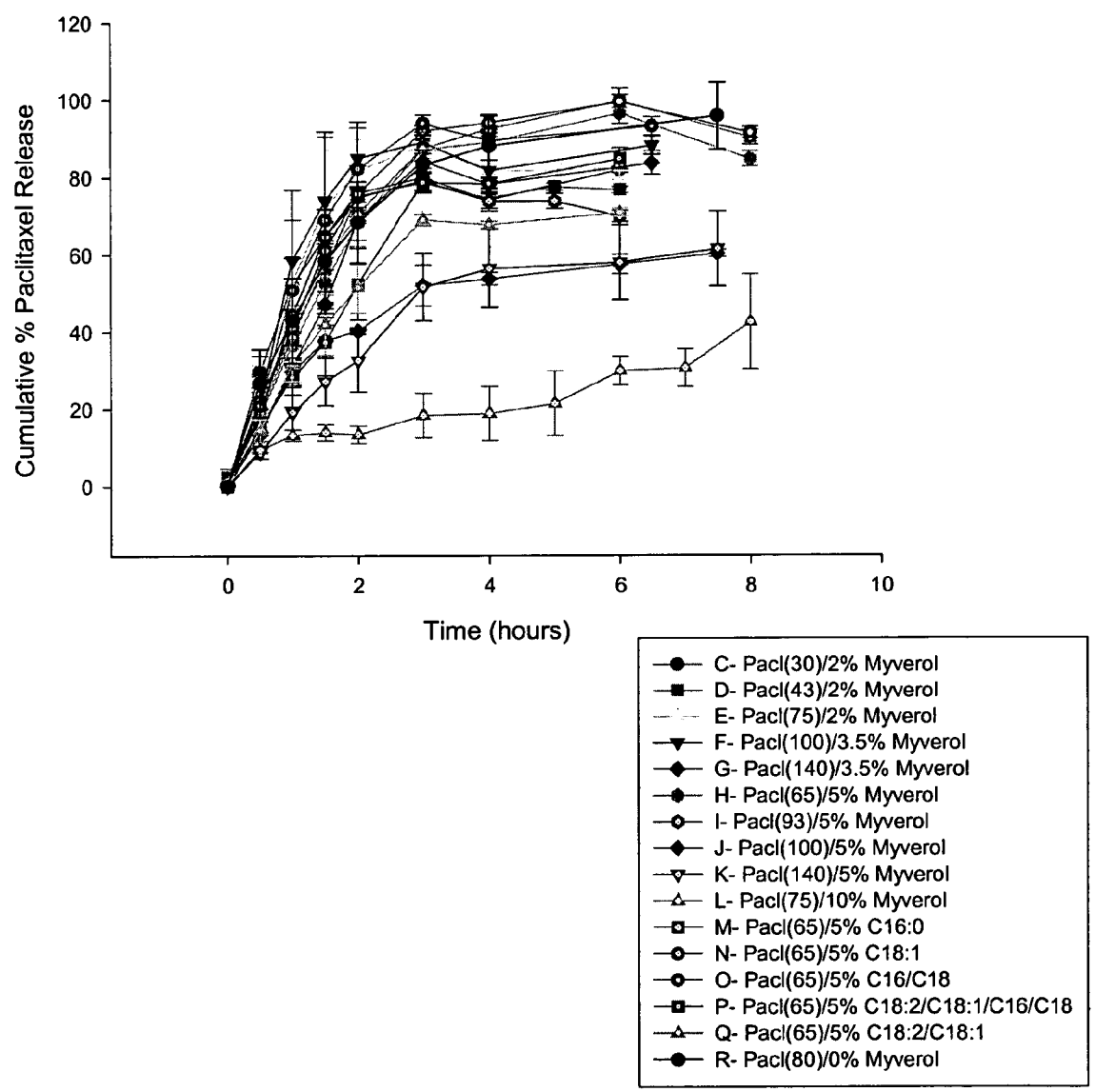
FIG. 1 compares the drug release profiles from drug delivery film compositions using the simple drug release method described in Example 2.

Unless indicated otherwise, all ingredient amounts expressed in percentage terms are presented as % w/w.

The drug delivery film compositions of the present invention contain (i) a water-soluble, film-forming polymer and (ii) a fatty acid glyceride or ester. Water-soluble, film-forming polymers are known and include, but are not limited to, hydroxypropyl cellulose, polyvinyl alcohol, polyacrylic acid, hydroxypropylmethyl cellulose, carboxymethyl cellulose, and hydroxyethyl cellulose. Such polymers are commercially available or can be made by methods known in the art. Preferred water-soluble, film-forming polymers are hydroxypropyl cellulose, polyvinyl alcohol, and carboxymethyl cellulose. The most preferred water-soluble, film-forming polymer for use in the drug delivery film compositions of the present invention is hydroxypropyl cellulose. In general, the drug delivery film compositions of the present invention will contain an amount of water-soluble, film-forming polymer equal to 25-99.5% of the total composition weight.

As used herein, "water-soluble, film-forming polymer" does not include polymers that are only biodegradeable but not water soluble, such as polyanhydrides and polylactides (e.g., polylactic glycolic acid or "PLGA"), nor polymers that are neither biodegradable not water-soluble, such as ethyl vinyl acetate.

Preferably, the only polymeric ingredient contained within the compositions of the present invention is a water-soluble, film-forming polymer.

In addition to the water-soluble, film-forming polymer, the compositions of the present invention also contain a fatty acid glyceride or ester having a molecular weight of 150-4000, wherein the fatty acid glyceride or ester has the formula below.

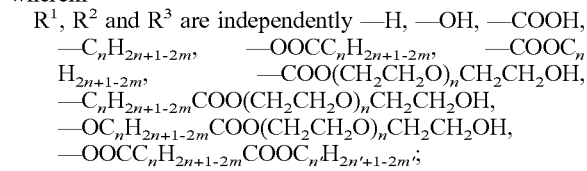

wherein
R$^1$, R$^2$ and R$^3$ are independently —H, —OH, —COOH, —C$_n$H$_{2n+1-2m}$, —OOCC$_n$H$_{2n+1-2m}$, —COOC$_n$H$_{2n+1-2m}$, —COO(CH$_2$CH$_2$O)$_n$CH$_2$CH$_2$OH, —C$_n$H$_{2n+1-2m}$COO(CH$_2$CH$_2$O)$_n$CH$_2$CH$_2$OH, —OC$_n$H$_{2n+1-2m}$COO(CH$_2$CH$_2$O)$_n$CH$_2$CH$_2$OH, —OOCC$_n$H$_{2n+1-2m}$COOC$_n$H$_{2n'+1-2m'}$;
n and n' are independently 0-50; and
m and m' are independently 0-10.

Fatty acid glycerides and esters of formula (I) are known. Such compounds are commercially available or can be made by methods known in the art. For example, mono-, di-, and triglyceride compounds are commercially available from such suppliers as NuChek Prep (Elysian, Minn.), Quest International (Hoffman Estates, Ill.) and Eastman Chemical Company (Kingsport, Tenn.), which produces such compounds under the Myverol® and Myvace® brands, and Gattefosse (Saint-Priest, France), which produces such compounds under the Gelucire®, Suppocire™, Ovucire™, and Monosteo® brands.

Preferred are the compounds of formula (I) wherein $R^1$, $R^2$ and $R^3$ are independently —H, —OH, —COOH, —$C_nH_{2n+1-2m}$, or —$OOCC_nH_{2n+1-2m}$; n and n' are independently 0-25; and m and m' are independently 0-3.

One commercially available fatty acid glyceride of formula (I) for use in the drug delivery film compositions of the present invention is the monoglyceride commercially available as Myverol® 18-92, available from Eastman Chemical Company. Myverol® 18-92, a distilled product of the glycerolysis of refined sunflower oil, has the following fatty acid distribution according to its manufacturer: 7.0% glyceryl monopalmitate (C16:0), 4.5% glyceryl monostearate (C18:0), 18.7% glyceryl monooleate (C18:1), and 67.5% glyceryl monolinoleate (C18:2).

Preferably, the drug delivery film compositions of the present invention contain a single fatty acid glyceride or mixture of fatty acid glycerides of formula (I) having a melting point $\leq 46°$ C. Most preferably, the single fatty acid glyceride or mixture of fatty acid glycerides of formula (I) has a melting point $\leq 42°$ C.

The drug delivery film compositions contain an amount of a fatty acid glyceride or ester ingredient equal to 0.5-25% of the weight of the water-soluble, film-forming polymer. Preferably, the amount of the fatty acid glyceride or ester ingredient in the drug delivery film compositions is equal to 1-10% of the weight of the water-soluble, film-forming polymer. Most preferably, the amount of fatty acid glyceride or ester ingredient is equal to 3-5% of the weight of the water-soluble, film-forming polymer.

The drug delivery film compositions of the present invention also comprise an ophthalmically acceptable drug. Such drugs include, but are not limited to, antibiotic, anti-inflammatory, anti-glaucoma, and anti-proliferative drugs. A preferred drug is paclitaxel. The amount of drug contained within the compositions of the present invention will vary depending upon the nature and severity of the condition to be treated, as well as the site of implantation in the patient and the identity of the drug. In general, however, the drug delivery film will contain an amount of drug equal to 0.0001-25% of the drug delivery film composition.

In addition to (i) an ophthalmic drug, (ii) a water-soluble, film-forming polymer, and (iii) a fatty acid glyceride or ester of formula (I) having a molecular weight of 150-4000, the drug delivery film compositions of the present invention optionally comprise one or more excipients. Many excipients for pharmaceutical compositions are known. Examples of suitable excipients include, but are not limited to: surfactants and stabilizers. Suitable surfactants include tyloxapol, polysorbate 20, polysorbate 60, polysorbate 80, and polyethoxylated castor oil derivatives (such as Cremophor EL and HCO-40). Suitable stabilizers include chelating agents, such as edetate disodium, and antioxidants, such as ascorbic acid and citric acid.

The compositions may be fashioned into a film of any shape suitable for insertion into the eye. Such shapes include, but are not limited to circular, rectangular, square and triangular shapes. For example, where the drug delivery film compositions of the present invention contain paclitaxel and are intended for use in glaucoma filtration surgery, the film may be fashioned as a 4.8 mm$^2$ disc that is 0.1-0.6 mm in height.

In one embodiment, the compositions of the present invention are used in connection with penetrating (e.g., trabeculectomy) and non-penetrating (e.g., viscocanalostomy) glaucoma filtration surgery. The label "penetrating" or non-penetrating" refers to whether the surgery involves penetrating into the anterior chamber. As part of both types of glaucoma filtration surgery, a bleb is surgically created as a reservoir for the outflow of aqueous humor. After the bleb is surgically created, a drug delivery film of the present invention containing an anti-proliferative drug is placed in the bleb to maintain bleb function by reducing or eliminating tissue growth or wound healing that would close the bleb. Preferably, the film contains the anti-proliferative drug paclitaxel in an amount such that the film delivers a total dose of 80-100 µg to a patient. In an especially preferred embodiment, the film is a 4.8 mm$^2$ disc that is 0.4-0.6 mm in height and contains 0.5-1% (w/w) of paclitaxel. Preferably, the drug delivery film of the present invention is used in connection with non-penetrating glaucoma filtration surgery.

The drug delivery film compositions of the present invention are particularly suitable for use as subconjunctival or sub-Tenon's implants, but also may be used in other locations within the eye, including intravitreal locations.

The following examples are intended to illustrate, but not limit, the present invention.

Example 1

Two different paclitaxel films were prepared by dissolving hydroxypropyl cellulose (HPC), Mvyerol 18-92 and paclitaxel in methanol. The solution was placed in a container and films (in the shape of discs) were obtained by evaporating methanol. The composition and size of these two films are shown in Table 1.

TABLE 1

|  | Film A | Film B |
| --- | --- | --- |
| Composition (W/W %) | 0.84% paclitaxel 99.16% HPC | 0.82% paclitaxel 1.94% Myverol 18-92 97.24% % HPC |
| Solvent Used for Film Preparation | Methanol | Methanol |
| Average Weight of film disks | 9.60 ± 0.43 mg | 10.03 ± 0.50 mg |
| Average thickness of film disks | 0.45-0.50 mm | 0.45-0.50 mm |
| Diameter of Film Disks | 4.8 mm | 4.8 mm |

Example 2

Figure 2:
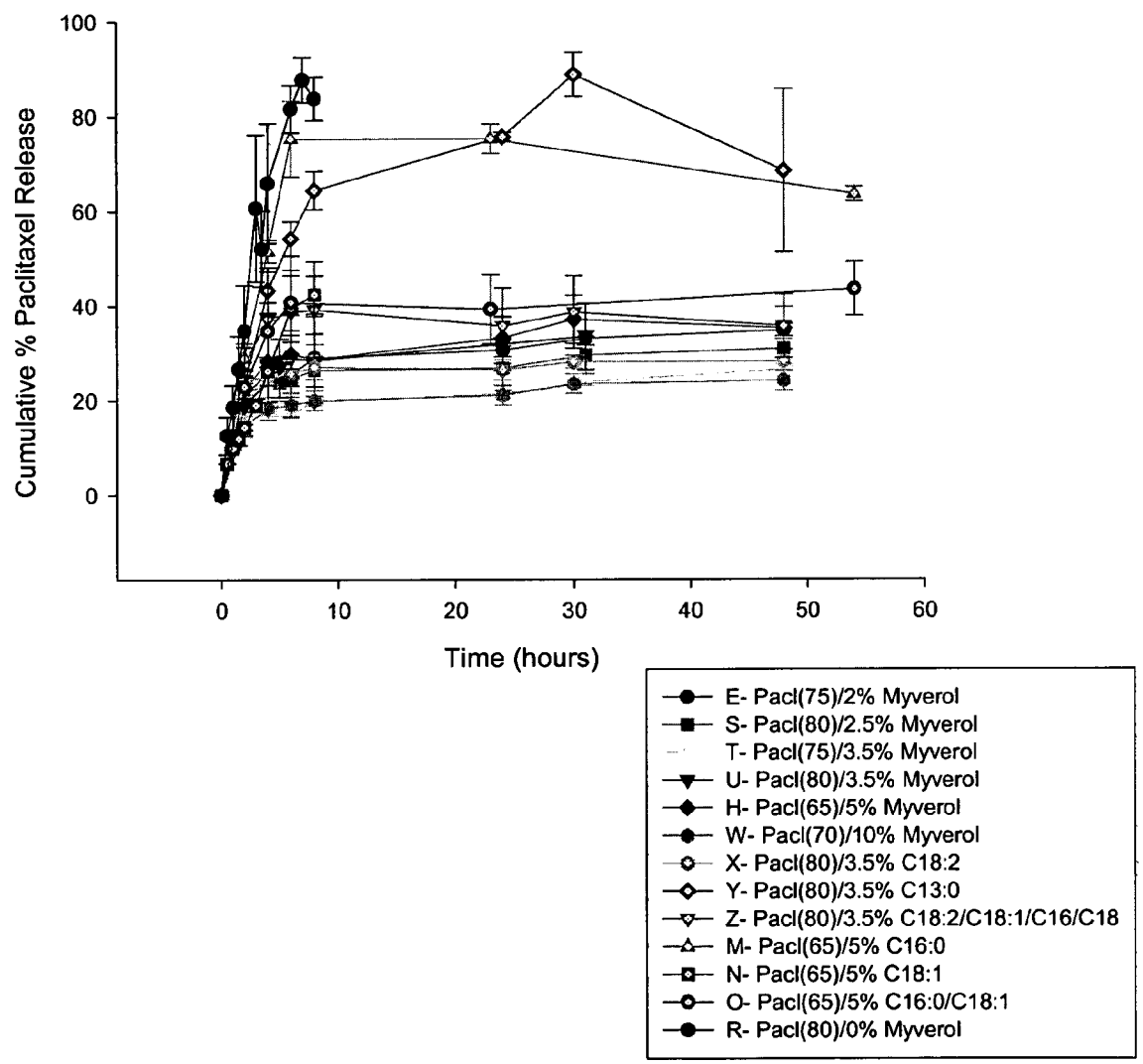
FIG. 2 compares the drug release profiles from drug delivery film compositions using the more sensitive drug release method described in Example 3.

Sixteen different paclitaxel films were prepared (using the same method described in Example 1) and evaluated in a simple drug release model for paclitaxel release. All sixteen films contained HPC as the only water-soluble, film-forming polymer. The remainder of the composition of the sixteen films is shown below in Table 2. Circular disks (approx. 0.35-0.55 mm in thickness; approx. 4.8 mm in diameter) were punched or cut out of each film and placed in plastic bottles containing 80 ml of phosphate buffered saline solution as a dissolution medium. The bottles were capped and placed in a reciprocal shaker at room temperature (shaking speed=100 rpm). At each sampling interval, 0.5 ml of dissolution medium was removed and immediately mixed with 0.5 ml of methanol to stabilize the drug. The amount of drug in the dissolution medium was determined using HPLC. The results are shown in FIG. 2 (n=6 for R, n=3 for all other film samples).

TABLE 2

| Film Sample | Paclitaxel (µg) | Amount of Fatty Acid Glyceride (% of wt. of HPC) | Fatty Acid Glyceride |
|---|---|---|---|
| C | 30 | 2 | Myverol 18-92 |
| D | 43 | 2 | Myverol 18-92 |
| E | 75 | 2 | Myverol 18-92 |
| F | 100 | 3.5 | Myverol 18-92 |
| G | 140 | 3.5 | Myverol 18-92 |
| H | 65 | 5 | Myverol 18-92 |
| I | 93 | 5 | Myverol 18-92 |
| J | 100 | 5 | Myverol 18-92 |
| K | 140 | 5 | Myverol 18-92 |
| L | 75 | 10 | Myverol 18-92 |
| M | 65 | 5 | C16:0 |
| N | 65 | 5 | C18:1 |
| O | 65 | 5 | C16:0 & C18:1 |
| P | 65 | 5 | C18:2, C18:1, C16:0 & C18:0 |
| Q | 65 | 5 | C18:2, C18:1 |
| R | 80 | 0 | None |

C16:0 = glyceryl monopalmitate
C18:0 = glyceryl monostearate
C18:1 = glyceryl monooleate
C18:2 = glyceryl monolinoleate As shown in FIG. 1, this simple drug release model did not distinguish the different film samples from each other very well. For example, the film with 0% of fatty acid glyceride (Sample R) showed a release profile in approximately the middle of the other film sample. A more sensitive and more representative methods developed.

Example 3

Thirteen different paclitaxel films were prepared (using the same method described in Example 1) and evaluated in a more sensitive, more representative drug release model for paclitaxel release. All thirteen films contained HPC as the only water-soluble, film-forming polymer. The remainder of the composition of the films is shown below in Table 3. Circular disks (approx. 0.35-0.55 mm in thickness; approx. 4.8 mm in diameter) were punched or cut out of each film and placed in separate dialysis tubes having a molecular weight cut-off of 12-14,000. After sealing the ends of the dialysis tubes, they were placed in plastic bottles containing 80 ml of phosphate buffered saline solution as a dissolution medium. The bottles were capped and placed in a reciprocal shaker at room temperature (shaking speed=100 rpm). At each sampling interval, 0.5 ml of dissolution medium was removed and immediately mixed with 0.5 ml of methanol to stabilize the drug. The amount of drug in the dissolution medium was determined using HPLC. The results are shown in FIG. 2 (n=6 for R, n=3 for all other film samples). This method is believed to more closely represent actual implant conditions, particularly when the drug delivery films of the present invention are implanted in the subconjunctival or sub-Tenon's locations.

TABLE 3

| Film Sample | Paclitaxel (µg) | Amount of Fatty Acid Glyceride (% of wt. of HPC) | Fatty Acid Glyceride |
|---|---|---|---|
| E | 75 | 2 | Myverol 18-92 |
| S | 80 | 2.5 | Myverol 18-92 |

TABLE 3-continued

| Film Sample | Paclitaxel (µg) | Amount of Fatty Acid Glyceride (% of wt. of HPC) | Fatty Acid Glyceride |
|---|---|---|---|
| T | 75 | 3.5 | Myverol 18-92 |
| U | 80 | 3.5 | Myverol 18-92 |
| H | 65 | 5 | Myverol 18-92 |
| W | 70 | 10 | Myverol 18-92 |
| X | 80 | 3.5 | C18:2 |
| Y | 80 | 3.5 | C13:0 |
| Z | 80 | 3.5 | C18:2, C18:1, C16:0 & C18:0 |
| M | 65 | 5 | C16:0 |
| N | 65 | 5 | C18:1 |
| O | 65 | 5 | C16:0 & C18:1 |
| R | 80 | 0 | None |

Figure 3:
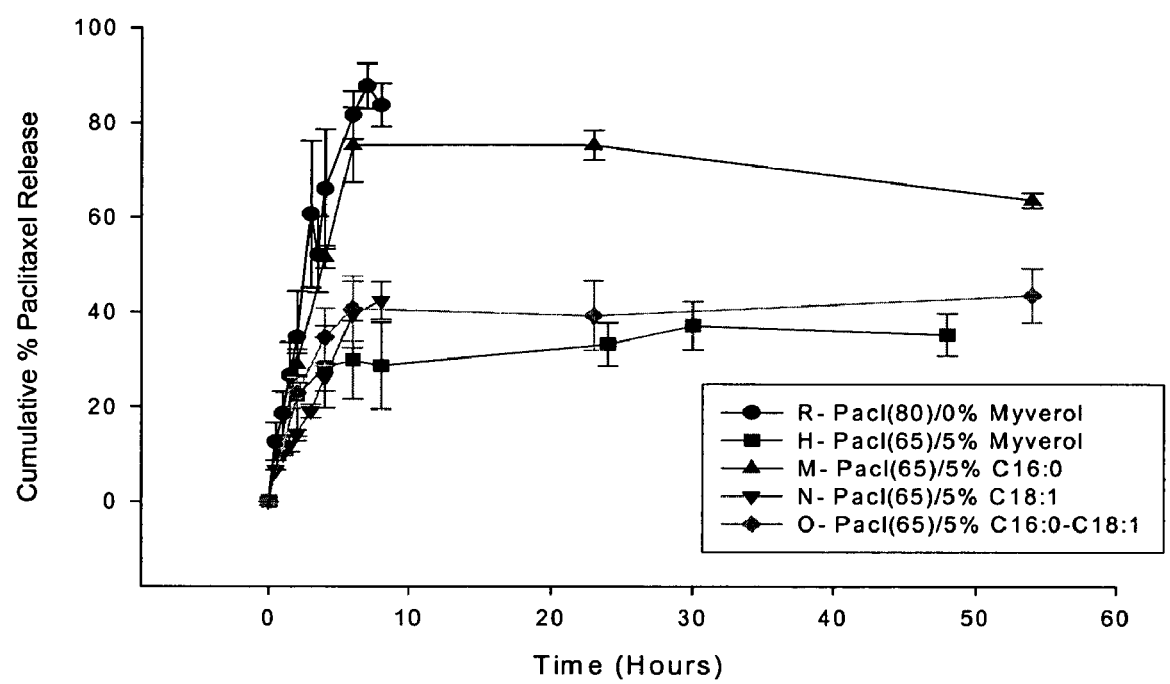
FIG. 3 compares the drug release profiles from five drug delivery film compositions: four compositions containing the same amount of different fatty acid glyceride ingredients and one composition containing no fatty acid glyceride ingredient (Samples H, M, N, O and R).

C13:0 = glyceryl monotridecanoate
C16:0 = glyceryl monopalmitate
C18:0 = glyceryl monostearate
C18:1 = glyceryl monooleate
C18:2 = glyceryl monolinoleate Additionally, the cumulative amount of drug release from the sample ("% cumulative release") is plotted against time in FIG. 3 for five samples (Samples H, M, N, O, and R). This graph compares the drug release profiles from compositions containing the same amount of different fatty acid glyceride ingredients.

Figure 4:
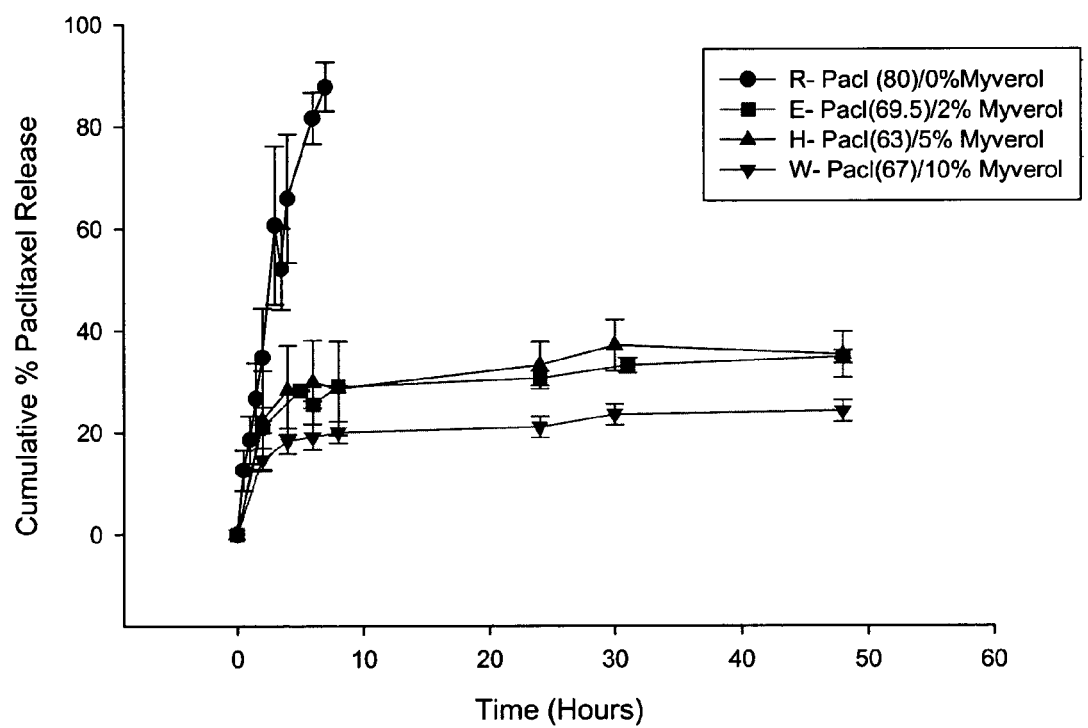
FIG. 4 compares the drug release profiles from four drug delivery film compositions containing varying amounts of the same fatty acid glyceride ingredient (Samples E, H, W and R).

FIG. 4 illustrates the effect of the fatty acid glyceride on the release profile: the higher the concentration of the fatty acid glyceride, the slower the release of drug. This graph compares the drug release profiles from four drug delivery film compositions containing varying amounts of the same fatty acid glyceride ingredient (Samples E, H, W and R).

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A bioerodible drug delivery film composition comprising (i) an ophthalmically acceptable drug, (ii) a water-soluble, film-forming polymer and (iii) a fatty acid glyceride or ester having a molecular weight of 150-4000, wherein the fatty acid glyceride or ester has the formula

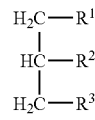

(I)

wherein
$R^1$, $R^2$ and $R^3$ are independently —H, —OH, —COOH, —$C_nH_{2n+1-2m}$, —OOC$_nH_{2n+1-2m}$, —COOC$_n$H$_{2n+1-2m}$, —COO(CH$_2$CH$_2$O)$_n$CH$_2$CH$_2$OH, —C$_n$H$_{2n+1-2m}$COO(CH$_2$CH$_2$O)$_n$CH$_2$CH$_2$OH, —OC$_n$H$_{2n+1-2m}$COO(CH$_2$CH$_2$O)$_n$CH$_2$CH$_2$OH, —OOCC$_n$H$_{2n+1-2m}$COOC$_n$H$_{2n'+1-2m'}$;
n and n' are independently 0-50; and
m and m' are independently 0-10,
wherein the film composition comprises 90-99.5% (w/w) of the water-soluble, film-forming polymer, and wherein the bioerodible drug delivery film composition comprises an amount of the fatty acid glyceride or ester equal to 0.5-10% of the weight of the water-soluble, film-forming polymer, and wherein said bioerodible drug delivery film composition is a solid film and has a shape suitable for insertion into an eye, and wherein said solid film contains said ophthalmically acceptable drug.

2. The film composition of claim 1 wherein the water-soluble, film forming polymer is selected from the group consisting of hydroxypropyl cellulose; polyvinyl alcohol; polyacrylic acid; hydroxypropylmethyl cellulose; carboxymethyl cellulose; and hydroxyethyl cellulose.

3. The film composition of claim 2 wherein the water-soluble, film forming polymer is selected from the group consisting of hydroxypropyl cellulose; polyvinyl alcohol; and carboxymethyl cellulose.

4. The film composition of claim 3 wherein the water-soluble, film forming polymer is hydroxypropyl cellulose.

5. The film composition of claim 1 wherein the film composition consists of (i) an ophthalmically acceptable drug, (ii) a water-soluble, film-forming polymer and (iii) a fatty acid glyceride or ester.

6. The film composition of claim 1 wherein
$R^1$, $R^2$ and $R^3$ are independently —H, —OH, —COOH, —$C_nH_{2n+1-2m}$, or —$OOCC_nH_{2n+1-2m}$;
n and n' are independently 0-25; and
m and m' are independently 0-3.

7. The film composition of claim 1 wherein the composition comprises a single fatty acid glyceride or mixture of fatty acid glycerides of formula (I) having a melting point ≦46° C.

8. The film composition of claim 1 wherein the composition comprises a single fatty acid glyceride or mixture of fatty acid glycerides of formula (I) having a melting point ≦42° C.

9. The film composition of claim 1 wherein the film composition comprises an amount of the fatty acid glyceride or ester equal to 1-10% of the weight of the water-soluble, film-forming polymer.

10. The film composition of claim 9 wherein the film composition comprises an amount of the fatty acid glyceride or ester equal to 3-5% of the weight of the water-soluble, film-forming polymer.

11. The film composition of claim 1 wherein the film composition comprises 0.5-1% (w/w) of the ophthalmically acceptable drug and the ophthalmically acceptable drug is paclitaxel.

12. The film composition of claim 1 wherein the film composition comprises an excipient selected from the group consisting of surfactants; chelating agents and antioxidants.

13. A method of treating an ophthalmic disease with an ophthalmically acceptable drug wherein the method comprising inserting into the eye the bioerodible drug delivery film composition of claim 1, and comprising (i) an ophthalmically acceptable drug, (ii) a water-soluble, film-forming polymer and (iii) a fatty acid glyceride or ester having a molecular weight of 150-4000, wherein the fatty acid glyceride or ester has the formula

wherein
$R^1$, $R^2$ and $R^3$ are independently —H, —OH, —COOH, —$C_nH_{2n+1-2m}$, —$OOCC_nH_{2n+1-2m}$, —$COOC_nH_{2n+1-2m}$, —$COO(CH_2CH_2O)_nCH_2CH_2OH$, —$C_nH_{2n+1-2m}COO(CH_2CH_2O)_nCH_2CH_2OH$, —$OOCC_nH_{2n+1-2m}COOC_{n'}H_{2n'+1-2m'}$;
n and n' are independently 0-50; and
m and m' are independently 0-10.

14. The method of claim 13 wherein the film composition is inserted into the eye as a subconjunctival or sub-Tenon's implant.

15. The method of claim 13 wherein the ophthalmically acceptable drug is an antiproliferative drug and the drug delivery film composition is used in connection with glaucoma filtration surgery.

16. The method of claim 15 wherein the drug delivery film composition is used in connection with non-penetrating glaucoma filtration surgery.

17. The bioerodible drug delivery film composition of claim 1, wherein said bioerodible drug delivery film composition consists essentially of said ophthalmically acceptable drug, said water-soluble, film-forming polymer, and said fatty acid glyceride or acid ester.

18. The bioerodible drug delivery film composition of claim 1, wherein said bioerodible drug delivery film composition consists of said ophthalmically acceptable drug, said water-soluble, film-forming polymer, and said fatty acid glyceride or ester, wherein said bioerodible drug delivery film composition has a drug delivery release profile of over 10 hours.

19. The bioerodible drug delivery film composition of claim 1, wherein said bioerodible drug delivery film composition has a drug delivery release profile of over 10 hours.

20. The bioerodible drug delivery film composition of claim 1, wherein said ophthalmically acceptable drug is released over time to provide a drug release profile that is greater than said bioerodible drug delivery film composition without said fatty acid glyceride or ester present.

* * * * *